(12) United States Patent
Chassot et al.

(10) Patent No.: US 7,641,702 B2
(45) Date of Patent: *Jan. 5, 2010

(54) O-AMINOPHENOL DERIVATIVES AND COLORANTS CONTAINING SAID COMPOUNDS

(75) Inventors: Laurent Chassot, La Chapellenie (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/572,143

(22) PCT Filed: May 18, 2005

(86) PCT No.: PCT/EP2005/005380

§ 371 (c)(1),
(2), (4) Date: May 20, 2008

(87) PCT Pub. No.: WO2006/007896

PCT Pub. Date: Jan. 26, 2006

(65) Prior Publication Data

US 2008/0235882 A1    Oct. 2, 2008

(30) Foreign Application Priority Data

Jul. 20, 2004   (DE) ................. 10 2004 035 164

(51) Int. Cl.
*A61Q 5/10* (2006.01)

(52) U.S. Cl. .................. 8/405; 8/406; 8/410; 8/412; 8/421; 8/435

(58) Field of Classification Search ........ 8/405, 8/406, 410, 411, 412, 421, 435
See application file for complete search history.

(56) References Cited

U.S. PATENT DOCUMENTS 4,396,392 A    8/1983   Konrad 6,840,965 B2 *    1/2005   Chassot et al. ............. 8/405
2003/0110577 A1 *    6/2003   Chassot et al. ............. 8/405

FOREIGN PATENT DOCUMENTS

| DE | 28 33 989 | | 2/1980 |
| WO | WO 03/018571 | A1 * | 3/2003 |
| WO | 2004/041226 | | 5/2004 |

OTHER PUBLICATIONS

STIC Search Report dated Sep. 9, 2008.*
* cited by examiner

*Primary Examiner*—Eisa B Elhilo
(74) *Attorney, Agent, or Firm*—Michael J. Striker

(57) ABSTRACT o-Aminophenol derivatives of the general formula (I) or physiologically compatible, water-soluble salts thereof,

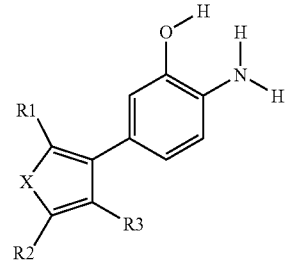

in which
X is oxygen, sulfur or N—R4;
R1, R2, R3 may be identical or different and, independently of one another, are hydrogen, a halogen atom, a cyano group, a $C_1$-$C_4$-alkoxy group, a $C_1$-$C_6$-alkyl group, a $C_1$-$C_4$-alkyl thioether group, a mercapto group, a nitro group, a trifluoromethane group, a —C(O)H group, a —C(O)CH$_3$ group, a —C(O)CF$_3$ group, an —Si(CH$_3$)$_3$ group, a $C_1$-$C_4$-hydroxyalkyl group or an aminomethyl group;
R4 is hydrogen, a $C_1$-$C_6$-alkyl group, a $C_1$-$C_4$-hydroxy-alkyl group, a phenyl group or an acetyl group;
and colorants containing said compounds for keratin fibers.

5 Claims, No Drawings

O-AMINOPHENOL DERIVATIVES AND COLORANTS CONTAINING SAID COMPOUNDS

CROSS-REFERENCE TO RELATED APPLICATIONS

This application is the national stage entry of PCT/EP05/05380, filed 18 May 2005 and claims priority under 35 U.S.C. 119(a)-(d) to German Patent Application DE 10 2004 035 164.3, filed 20 Jul. 2004.

BACKGROUND OF THE INVENTION

1. Field of the Invention

The invention relates to novel o-aminophenol derivatives and to agents containing said compounds for coloring keratin fibers.

2. Description of Related Art

In the field of coloring keratin fibers, in particular hair coloring, oxidation dyes have achieved significant importance. The coloration arises here as a result of the reaction of certain developer substances with certain coupler substances in the presence of a suitable oxidizing agent. The developer substances used here are, in particular, 2,5-diaminotoluene, 2,5-diaminophenylethyl alcohol, p-aminophenol, 1,4-diaminobenzene and 4,5-diamino-1-(2-hydroxyethyl)pyrazole, while examples of coupler substances are resorcinol, 2-methylresorcinol, 1-naphthol, 3-aminophenol, m-phenylenediamine, 2-amino-4-(2'-hydroxyethyl)aminoanisole, 1,3-diamino-4-(2'-hydroxyethoxy)benzene and 2,4-diamino-5-fluorotoluene.

Besides the stability of the colorations over at least 4 to 6 weeks, numerous additional requirements are placed on oxidation dyes that are used for coloring human hair. For example, the dyes must be acceptable from a toxicological and dermatological point of view, and the hair colorations achieved should have good light fastness, permanent wave fastness, rubbing fastness and stability to shampooing, and also adequate resistance to perspiration excretions. Furthermore, it is required that, by combining suitable developer substances and coupler substances, a broad palette of different color nuances can be produced.

A particular problem when nuancing relatively light color tones is the even absorption of dye from the hair roots to the hair ends, and also the durability of the nuances to a permanent wave treatment. The use of direct yellow-coloring aromatic nitro dyes together with oxidative hair color precursors can solve the described problem in part, but the stability of the colorations over a period of several weeks is often unsatisfactory.

To solve the described problem, DE-A 28 33 989 proposes the use of 6-amino-3-methylphenol as oxidative yellow coloring agent in oxidative hair colorants. This compound is said to have good suitability as nuancing dye for producing light blond tones and gold tones, although the set requirements are not completely satisfied particularly with regard to the stability of the hair colorations to the effect of permanent waving compositions.

BRIEF SUMMARY OF THE INVENTION

It has now been found that certain o-aminophenol derivatives according to the general formula (I) satisfy the requirements placed on color components to a particularly high degree. Thus, when using these o-aminophenol derivatives in an oxidizing medium, color nuances are obtained which are extraordinarily wash-fast and perm-stable.

DETAILED DESCRIPTION OF THE INVENTION

The present invention therefore provides o-aminophenol derivatives of the general formula (I) or physiologically compatible, water-soluble salts thereof,

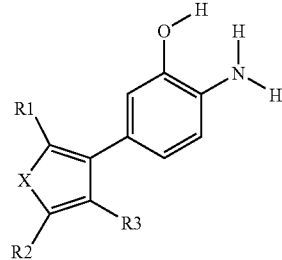

in which
X is oxygen, sulfur or N—R4;
R1, R2, R3 may be identical or different and, independently of one another, are hydrogen, a halogen atom, a cyano group, a $C_1$-$C_4$-alkoxy group, a $C_1$-$C_6$-alkyl group, a $C_1$-$C_4$-alkyl thioether group, a mercapto group, a nitro group, a trifluoromethane group, a —C(O)H group, a —C(O)CH$_3$ group, a —C(O)CF$_3$ group, an —Si(CH$_3$)$_3$ group, a $C_1$-$C_4$-hydroxyalkyl group or an aminomethyl group;
R4 is hydrogen, a $C_1$-$C_6$-alkyl group, a $C_1$-$C_4$-hydroxyalkyl group, a phenyl group or an acetyl group.

Compounds of the formula (I) which may be mentioned are, for example, the following compounds: 2-amino-5-(3-thienyl)phenol, 2-amino-5-(3-furyl)phenol, 2-amino-5-(pyrrol-3-yl)phenol, 2-amino-5-(2-chloro-3-thienyl)phenol, 2-amino-5-(2-cyano-3-thienyl)phenol, 2-amino-5-(2-ethyl-3-thienyl)phenol, 2-amino-5-(2-formyl-3-thienyl)phenol, 2-amino-5-(2-methyl-3-thienyl)phenol, 2-amino-5-(2-trifluoromethyl-3-thienyl)phenol, 2-amino-5-(4-chloro-3-thienyl)phenol, 2-amino-5-(4-cyano-3-thienyl)phenol, 2-amino-5-(4-ethyl-3-thienyl)phenol, 2-amino-5-(4-formyl-3-thienyl)phenol, 2-amino-5-(4-methyl-3-thienyl)phenol, 2-amino-5-(4-trifluoromethyl-3-thienyl)phenol, 2-amino-5-(5-chloro-3-thienyl)phenol, 2-amino-5-(5-cyano-3-thienyl)phenol, 2-amino-5-(5-ethyl-3-thienyl)phenol, 2-amino-5-(5-formyl-3-thienyl)phenol, 2-amino-5-(5-methyl-3-thienyl)phenol, 2-amino-5-(5-trifluoromethyl-3-thienyl)phenol, 2-amino-5-(2-dimethylaminomethyl-3-thienyl)phenol, 2-amino-5-(4-dimethylaminomethyl-3-thienyl)phenol, 2-amino-5-(2-bis(2-hydroxyethyl)aminomethyl-3-thienyl)phenol, 2-amino-5-(4-bis(2-hydroxyethyl)aminomethyl-3-thienyl)phenol and physiologically compatible salts thereof.

Preference is given to compounds of the formula (I) in which (i) X is sulfur and/or (ii) one of the groups R2, R3 or R4 is hydrogen, a methyl group, or a chlorine atom and the two other radicals are hydrogen.

Particular preference is given to the following compounds of the formula (I): 2-amino-5-(3-thienyl)phenol, 2-amino-5-(2-methyl-3-thienyl)phenol, 2-amino-5-(5-chloro-3-thienyl)phenol, 2-amino-5-(2-formyl-3-thienyl)phenol, 2-amino-5-(4-formyl-3-thienyl)phenol and physiologically compatible salts thereof.

The compounds of the formula (I) can be used either in the form of free bases or else in the form of their physiologically compatible salts with inorganic or organic acids, such as, for example, hydrochloric acid, sulfuric acid, phosphoric acid, acetic acid, propionic acid, lactic acid or citric acid.

The o-aminophenol derivatives of the formula (I) according to the invention can be prepared using known synthesis methods; for example by a palladium(0) catalyzed coupling of a substituted benzene of the formula (II)

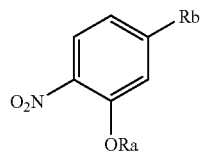
(II)

with a compound of the formula (III)

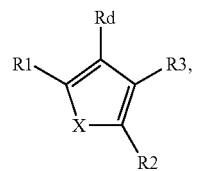
(III)

with subsequent reduction and cleavage of the protective group, where either Rb is a halogen atom and Rd has the meaning $B(OH)_2$, or Rb has the meaning $B(OH)_2$ and Rd is a halogen atom;

Ra is a protective group, as described, for example, in the chapter "Protective Groups" in Organic Synthesis, chapter 3, Wiley Interscience, 1991; and X, R1, R2 and R3 have the meaning given in formula (I).

The compounds of the formula (I) according to the invention permit colorations with excellent color fastness, particularly with regard to wash fastness and rubbing fastness and also perm fastness.

The present invention therefore further provides agents for the oxidative coloring of keratin fibers, such as, for example, hairs, furs, feathers or wool, in particular human hair, which comprise at least one o-aminophenol derivative of the formula (I).

The o-aminophenol derivative of the formula (I) is present in the colorant according to the invention in an amount of from about 0.001 to 5 percent by weight, where an amount of from about 0.005 to 2 percent by weight and in particular 0.01 to 1 percent by weight is preferred.

The compounds of the formula (I) color keratin fibers, in particular human hair, without the addition of further dyes in yellow color tones.

To achieve further color nuances, one or more customary oxidative dyes, for example developer substances or coupler substances, alone or in a mixture with one another, can be added.

Suitable coupler substances here are, in particular, N-(3-dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl) amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 1,3-diamino-4-(2,3-dihydroxypropoxy)benzene, 1,3-diamino-4-(3-hydroxypropoxy)benzene, 1,3-diamino-4-(2-methoxyethoxy)benzene, 2,4-diamino-1,5-di-(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di-(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy) propane, di(2,4-diaminophenoxy)methane, 1,3-diamino-2,4-dimethoxybenzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-4-methoxy-2-methylphenol, 5-[(2-hydroxyethyl)amino]-2-methylphenol, 3-[(2-hydroxyethyl) amino]phenol, 3-[(2-methoxyethyl)amino]phenol, 5-amino-2-ethylphenol, 5-amino-2-methoxyphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 2,6-dihydroxy-3,4-dimethylpyridine, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4 (2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole, 2,3-indolinedione.

Suitable developer substances are preferably 1,4-di-aminobenzene (p-phenylenediamine), 1,4-diamino-2-methylbenzene (p-tolylenediamine), 1,4-diamino-2,6-dimethylbenzene, 1,4-diamino-3,5-diethylbenzene, 1,4-diamino-2,5-dimethylbenzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)benzene, 4-(2,5-diaminophenyl)-2-((diethylamino)methyl)thiophene, 2-chloro-3-(2,5-diaminophenyl)thiophene, 1,4-diamino-2-(pyridin-3-yl)benzene, 2,5-diaminobiphenyl, 2,5-diamino-4'-(1-methylethyl)-1,1'-biphenyl, 2,3',5-triamino-1,1'-biphenyl, 1,4-diamino-2-methoxymethylbenzene, 1,4-diamino-2-aminomethylbenzene, 1,4-diamino-2-((phenylamino)methyl)benzene, 1,4-diamino-2-((ethyl-(2-hydroxyethyl)amino)methyl)benzene, 1,4-diamino-2-hydroxymethylbenzene, 1,4-diamino-2-(2-hydroxyethoxy)benzene, 2-(2-(acetylamino)ethoxy)-1,4-diaminobenzene, 4-phenylaminoaniline, 4-dimethylaminoaniline, 4-diethylaminoaniline, 4-dipropylaminoaniline, 4-[ethyl(2-hydroxyethyl)amino]aniline, 4-[di-(2-hydroxyethyl)amino]aniline, 4-[di(2-hydroxyethyl)-amino]-2-methylaniline, 4-[(2-methoxyethyl)amino]-aniline, 4-[(3-hydroxypropyl)amino]aniline, 4-[(2,3-dihydroxypropyl)amino]aniline, 4-(((4-aminophenyl)-methyl)amino)aniline, 4-[(4-aminophenylamino)methyl]-phenol, 1,4-diamino-N-(4-pyrrolidin-1-ylbenzyl) benzene, 1,4-diamino-N-furan-3-ylmethylbenzene, 1,4-diamino-N-thiophen-2-ylmethylbenzene, 1,4-diamino-N-furan-2-ylmethylbenzene, 1,4-diamino-N-thiophen-3-ylmethylbenzene, 1,4-diamino-N-benzylbenzene, 1,4-diamino-2-(1-hydroxyethyl)benzene, 1,4-diamino-2-(2-hydroxyethyl)benzene, 1,4-diamino-2-(1-methylethyl) benzene, 1,3-bis[(4-aminophenyl)(2-hydroxyethyl)amino]-2-propanol, 1,4-bis-[(4-aminophenyl)amino]butane, 1,8-bis (2,5-diaminophenoxy)-3,6-dioxaoctane, 2,5-diamino-4'-hydroxy-1,1'-biphenyl, 2,5-diamino-2'-trifluoromethyl-1,1'-biphenyl, 2,4',5-triamino-1,1'-biphenyl, 4-aminophenol, 4-amino-3-methylphenol, 4-amino-3-(hydroxymethyl)phenol, 4-amino-3-fluorophenol, 4-methylaminophenol, 4-amino-2-(aminomethyl)phenol, 4-amino-2-(hydroxymethyl)phenol, 4-amino-2-fluorophenol, 4-amino-2-[(2-hydroxyethyl)amino]methylphenol, 4-amino-2-methylphenol, 4-amino-2-(methoxymethyl)phenol, 4-amino-2-(2-hydroxyethyl)phenol, 5-aminosalicylic acid, 2,5-diaminopyridine, 2,4,5,6-tetraaminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 4,5-diamino-1-pentyl-1H-pyrazole, 4,5-diamino-1-(phenylmethyl)-1H-pyrazole, 4,5-diamino-1-((4-methoxyphenyl)methyl-1H-pyrazole, 2-aminophenol, 2-amino-6-methylphenol, 2-amino-5-methylphenol, 1,2,4-trihydroxybenzene, 2,4-diaminophenol, 1,4-dihydroxybenzene and 2-(((4-aminophenyl)amino)methyl)-1,4-diaminobenzene.

The total amount of the abovementioned developer substances and coupler substances in the agent according to the invention is about 0.01 to 12 percent by weight, in particular about 0.2 to 6 percent by weight.

In addition, the colorant according to the invention can additionally comprise other color components, for example 4-(2,5-diaminobenzylamino)aniline or 3-(2,5-diaminobenzylamino)aniline, and also customary natural, nature-identical or synthetic direct dyes from the group of anionic (acidic) and cationic (basic) dyes, triarylmethane dyes, nitro dyes, dispersion dyes and azo dyes, for example natural dyes such as indigo or henna, triphenylmethane dyes such as 4-[(4'-aminophenyl)(4'-imino-2''',5''-cyclohexadien-1''-ylidene) methyl]-2-methylaminobenzene monohydrochloride (C.I. 42 510) and 4-[(4'-amino-3'-methylphenyl) (4''-imino-3''-methyl-2'',5''-cyclohexadien-1''-ylidene)methyl]-2-methylaminobenzene monohydrochloride (C.I. 42 520), aromatic nitro dyes such as 4-(2'-hydroxyethyl)aminonitrotoluene, 2-amino-4,6-dinitrophenol, 2-amino-5-(2'-hydroxyethyl) aminonitrobenzene, 2-chloro-6-(ethylamino)-4-nitrophenol, 4-chloro-N-(2-hydroxyethyl)-2-nitroaniline, 5-chloro-2-hydroxy-4-nitroaniline, 2-amino-4-chloro-6-nitrophenol and 1-[(2'-ureidoethyl)amino-4-nitrobenzene, azo dyes such as 6-[(4'-aminophenyl)azo]-5-hydroxynaphthalene-1-sulfonic acid sodium salt (C.I. 14 805) and dispersion dyes such as, for example, 1,4-diaminoanthraquinone and 1,4,5,8-tetraaminoanthraquinone.

The colorant comprises the abovementioned other color components preferably in a total amount of from about 0.1 to 4 percent by weight.

Of course, the coupler substances and developer substances and also the other color components, if they are bases, can also be used in the form of their physiologically compatible salts with organic or inorganic acids, such as, for example, hydrochloric acid or sulfuric acid, or—if they have aromatic OH groups—in the form of the salts with bases, for example as alkali metal phenoxides.

Moreover, the colorants, if they are to be used for coloring hair, can also comprise further customary cosmetic additives, for example antioxidants such as ascorbic acid, thioglycolic acid or sodium sulfite, and also perfume oils, complexing agents, wetting agents, emulsifiers, thickeners and care substances.

The preparation form of the colorant according to the invention can, for example, be a solution, in particular an aqueous or aqueous-alcoholic solution, a paste, a cream, a gel, an emulsion or an aerosol preparation. Its composition is a mixture of the dye components with the additives customary for such preparations.

Customary additives in solutions, creams, emulsions or gels are, for example, solvents such as water, lower aliphatic alcohols, for example ethanol, propanol or isopropanol, glycerol or glycols such as 1,2-propylene glycol, also wetting agents or emulsifiers from the classes of anionic, cationic, amphoteric or nonionogenic surface-active substances such as, for example, fatty alcohol sulfates, oxyethylated fatty alcohol sulfates, alkylsulfonates, alkylbenzenesulfonates, alkyltrimethylammonium salts, alkylbetaines, oxyethylated fatty alcohols, oxyethylated nonylphenols, fatty acid alkanolamides and oxyethylated fatty acid esters, also thickeners such as higher fatty alcohols, starch, cellulose derivatives, petrolatum, paraffin oil and fatty acids, and also care substances such as cationic resins, lanolin derivatives, cholesterol, pantothenic acid and betaine. The constituents mentioned are used in the amounts customary for such purposes, for example the wetting agents and emulsifiers in concentrations of from about 0.5 to 30 percent by weight, the thickeners in an amount of from about 0.1 to 30 percent by weight and the care substances in a concentration of from about 0.1 to 5 percent by weight.

Depending on the composition, the colorant according to the invention can be weakly acidic, neutral or alkaline. In particular, it has a pH of from 6.5 to 11.5, basic adjustment being carried out preferably with ammonia or organic amines, for example monoethanolamine and triethanolamine, but also amino acids or inorganic bases such as sodium hydroxide and potassium hydroxide. It is likewise possible to use combinations of the abovementioned compounds, in particular a combination of ammonia and of monoethanolamine. For a pH adjustment in the acidic range, inorganic or organic acids, for example phosphoric acid, acetic acid, citric acid or tartaric acid, are suitable.

For use for the oxidative coloring of hair, the colorant described above is mixed directly prior to use with an oxidizing agent, and an amount of this mixture sufficient for the hair-coloring treatment, generally about 60 to 200 grams depending on the fullness of the hair, is applied to the hair.

Suitable oxidizing agents for developing the hair color are primarily hydrogen peroxide or its addition compounds onto urea, melamine, sodium borate or sodium carbonate in the form of a 3 to 12 percent strength, preferably 6 percent strength, aqueous solution, but also atmospheric oxygen. If a 6 percent strength hydrogen peroxide solution is used as oxidizing agent, then the weight ratio between hair colorant and oxidizing agent is 5:1 to 1:2, but preferably 1:1. Larger amounts of oxidizing agent are used primarily at higher dye concentrations in the hair colorant or if stronger bleaching of the hair is intended at the same time. The mixture is left to act on the hair at 15 to 50 degrees Celsius for about 10 to 45 minutes, preferably 30 minutes, then the hair is rinsed with water and dried. If necessary, this rinsing is followed by washing with a shampoo and, if required, after-rinsing with a weak organic acid, such as, for example, citric acid or tartaric acid. The hair is then dried.

The hair colorants according to the invention with a content of o-aminophenol derivatives of the formula (I) permit hair colorations with excellent color fastness, especially with regard to light fastness, wash fastness and rubbing fastness and also perm fastness. With regard to the coloring properties, the hair colorants according to the invention offer, depending on the nature and the composition of the color components, a broad pallet of different color nuances which ranges from blonde via brown, purple, violet to blue and black color tones. It is thus possible, for example by using a combination of the compounds of the formula (I) with 4-(2,5-diaminobenzylamino)aniline, to achieve blonde to brown hair colorations. Here, the color tones are characterized by their particular color intensity and a good color balance between damaged and undamaged hair. The very good coloring properties of the hair colorants according to the present application are further evident from the fact that these agents permit a coloring of gray, chemically nonpredamaged hair without problems and with good coverage.

The examples below are intended to illustrate the subject matter of the invention in more detail without limiting it thereto.

EXAMPLES

Examples 1

Synthesis of 2-amino-5-(3-thienyl)phenol

A. Synthesis of 4-chloro-2-(ethoxymethoxy)-1-nitrobenzene

A solution of 2.6 g (15 mmol) of 4-chloro-2-hydroxynitrobenzene in 30 ml of acetonitrile is admixed, at 0° C. and in portions, with 1 g (23 mmol) of a sodium hydride dispersion (55% in oil). The mixture obtained is then stirred for 50 minutes at 0° C. 1.8 g (18.5 mmol) of chloromethyl ethyl ether are then added and the mixture is stirred for 1 hour at 0° C. The reaction mixture is then poured onto ice, extracted with ethyl acetate and the organic phase is washed with a saturated aqueous sodium chloride solution, dried over $Na_2SO_4$ and, after filtration, concentrated by evaporation.

3.7 g of 4-chloro-2-(ethoxymethoxy)-1-nitrobenzene are obtained.
$^1$H NMR (300 MHz, DMSO-D6): δ=7.95 (d, 1H), 7.16 (dd, 1H), 7.55 (d, 1H), 7.24 (dd, 1H), 5.47 (s; 2H), 3.707 (q, 2H), 1.14 (t, 3H)

B. Synthesis of 2-nitro-5-(3-thienyl)phenol 4.6 g (20 mmol) of 4-chloro-2-(ethoxymethoxy)-1-nitrobenzene from stage A and 3.8 g (30 mmol) of 3-(thienyl) boric acid are dissolved in 80 ml of toluene under nitrogen. Then, 0.01 g (0.05 mmol) of palladium acetate, 0.035 g (1 mmol) of 2-(dicyclohexylphosphino)biphenyl and 1.5 g of tripotassium phosphate are added and the reaction mixture is heated to 80° C. When the reaction is complete, the reaction mixture is poured into 50 ml of ethyl acetate, and the organic phase is extracted with dilute sodium hydroxide solution and then dried with magnesium sulfate. The solvent is distilled off on a rotary evaporator and the residue is purified over silica gel with hexane/ethyl acetate (9:1).

The product obtained in this way is heated to 50° C. in 20 ml of ethanol. Subsequently, 10 ml of a 2.9 molar ethanolic hydrochloric acid solution are added dropwise and then the reaction mixture is cooled to 0° C. The precipitate is filtered off, washed twice with ethanol and then dried.

1.6 g of 2-nitro-5-(3-thienyl)phenol are obtained.
$^1$H NMR (300 MHz, DMSO-D6): δ=11 (s, 1H), 8.11 (dd, 1H), 7.98 (d, 1H), 7.72 (dd, 1H), 7.6 (dd; 1H), 7.45 (d, 1H), 7.39 (dd, 1H)

C. Synthesis of 2-amino-5-(3-thienyl)phenol hydrochloride 1.45 g (6.5 mmol) of 2-nitro-5-(3-thienyl)phenol from stage B are dissolved in 15 ml of ethanol and hydrogenated at 25° C. with addition of 0.3 g of a palladium-activated carbon catalyst (10% strength). After the required amount of hydrogen has been absorbed, the mixture is filtered off from the catalyst and the solvent is distilled off on a rotary evaporator.

0.55 g of 2-amino-5-(3-thienyl)phenol are obtained.
$^1$H NMR (300 MHz, DMSO-D6): δ=10.8 (s, 1H), 9.75 (b, 2H), 7.79 (dd, 1H), 7.65 (dd, 1H), 7.44 (dd, 1H), 7.33 (d; 1H), 7.30 (d, 1H), 7.21 (dd, 1H)

Examples 2 to 12

Hair Colorants

Hair-coloring solutions of the following composition are prepared:
X g 2-amino-5-(3-thienyl)phenol hydrochloride
U g developer substance E8 to E15 as in table 1
Y g coupler substance K12 to K35 as in table 2
Z g direct dye D2 to D3 as in table 2
10.0 g potassium oleate (8 percent strength aqueous solution)
10.0 g ammonia (22 percent strength aqueous solution)
10.0 g ethanol
0.3 g ascorbic acid
ad 100.0 g water
30 g of the above coloring solution are mixed directly prior to use with 30 g of a 6 percent strength aqueous hydrogen peroxide solution. The mixture is then applied to bleached hair. After a contact time of 30 minutes at 40° C., the hair is rinsed with water, washed with a standard commercial shampoo and dried. The coloring results are summarized in table 5.

Examples 13 to 18

Hair Colorants

Cream-like color carrier masses of the following composition are prepared:
X g 2-amino-5-(3-thienyl)phenol hydrochloride
U g developer substance E8 to E15 as in table 1
Y g coupler substance K12 to K35 as in table 3
Z g direct dye D2 to D3 as in table 2
15.0 g cetyl alcohol
0.3 g ascorbic acid
3.5 g sodium lauryl alcohol diglycol ether sulfate (28 percent strength aqueous solution)
3.0 g ammonia (22 percent strength aqueous solution)
0.3 g sodium sulfite, anhydrous
ad 100.0 g water
30 g of the above coloring cream are mixed directly prior to use with 30 g of a 6 percent strength hydrogen peroxide solution. The mixture is then applied to the hair. After a contact time of 30 minutes, the hair is rinsed with water, washed with a standard commercial shampoo and dried. The coloring results are summarized in table 6.

Examples 19 to 26

Hair Colorants

Hair-coloring solutions of the following composition are prepared:
- X g 2-amino-5-(3-thienyl)phenol hydrochloride
- Z g color component W1 or W2 as in table 4
- U g developer substance E8 to E15 as in table 1
- 10.0 g potassium oleate (8 percent strength aqueous solution)
- 10.0 g ammonia (22 percent strength aqueous solution)
- 10.0 g ethanol
- 0.3 g ascorbic acid
- ad 100.0 g water 30 g of the above coloring solution are mixed directly prior to use with 30 g of a 6 percent strength hydrogen peroxide solution. The mixture is then applied to bleached hair. After a contact time of 30 minutes at 40° C., the hair is rinsed with water, washed with a standard commercial shampoo and dried. The coloring results are given in table 7 below.

TABLE 1

Developer substances

| | |
|---|---|
| E8 | 1,4-Diaminobenzene |
| E9 | 2,5-Diaminophenylethanol sulfate |
| E10 | 3-Methyl-4-aminophenol |
| E11 | 4-Amino-2-aminomethylphenol dihydrochloride |
| E12 | 4-Aminophenol |
| E14 | 4,5-Diamino-1-(2'-hydroxyethyl)pyrazole sulfate |
| E15 | 2,5-Diaminotoluene sulfate |

TABLE 2

Direct dyes

| | |
|---|---|
| D2 | 6-Chloro-2-ethylamino-4-nitrophenol |
| D3 | 2-Amino-6-chloro-4-nitrophenol |

TABLE 3

Coupler substances

| | |
|---|---|
| K12 | 2-Amino-4-(2'-hydroxyethyl)aminoanisole sulfate |
| K13 | 1,3-Diamino-4-(2'-hydroxyethoxy)benzene sulfate |
| K16 | 3,5-Diamino-2,6-dimethoxypyridine dihydrochloride |
| K18 | N-(3-Dimethylamino)phenylurea |
| K21 | 3-Aminophenol |
| K22 | 5-Amino-2-methylphenol |
| K23 | 3-Amino-2-chloro-6-methylphenol |
| K25 | 1-Naphthol |
| K26 | 1-Acetoxy-2-methylnaphthalene |
| K31 | 1,3-Dihydroxybenzene |
| K32 | 2-Methyl-1,3-dihydroxybenzene |
| K33 | 1-Chloro-2,4-dihydroxybenzene |
| K35 | 3,4-Methylenedioxyphenol |

TABLE 4

Color components

| | |
|---|---|
| W1 | 4-(2,5-Diaminobenzylamino)aniline*HCl |
| W2 | 2-(3-Aminophenyl)aminomethyl-1,4-diaminobenzene*HCl |

TABLE 5

Hair colorants

| | Example No. | | | | |
|---|---|---|---|---|---|
| Dyes | 2 | 3 | 4 | 5 | 6 |
| | (Amount of dye in grams) | | | | |
| 2-Amino-5-(3-thienyl)phenol hydrochloride | 0.30 | 0.03 | 0.05 | 0.03 | 0.02 |
| E10 | | | | 0.55 | |
| E11 | | 0.55 | | | |
| E12 | | | 0.55 | | |
| E14 | | | | | 0.55 |
| K31 | | | | 0.18 | 0.20 |
| K32 | | 0.22 | | | |
| K33 | | | 0.20 | | |
| K25 | | 0.30 | | 0.30 | 0.30 |
| K26 | | | 0.35 | | |
| Color result | luminous yellow | red-brown | red-brown | red-brown | red-brown |

| | Example No. | | | | | |
|---|---|---|---|---|---|---|
| Dyes | 7 | 8 | 9 | 10 | 11 | 12 |
| | (Amount of dye in grams) | | | | | |
| 2-Amino-5-(3-thienyl)phenol hydrochloride | 0.010 | 0.006 | 0.020 | 0.005 | 0.050 | 0.010 |
| E9 | | | | | 0.096 | 1.800 |
| E10 | 0.096 | 0.240 | 0.300 | 0.900 | 0.010 | 0.700 |
| K12 | | | | | 0.010 | |
| K18 | | | | | | 0.030 |
| K21 | | | | | 0.020 | 0.060 |
| K22 | 0.080 | 0.200 | 0.250 | 0.056 | | 0.580 |
| K25 | | | | | 0.030 | |
| K31 | | | | 0.200 | | 0.800 |
| K32 | | 0.030 | 0.050 | 0.316 | | |
| K35 | 0.018 | | | | | |
| D2 | | | | | 0.010 | |
| D3 | 0.040 | 0.060 | 0.025 | | | |
| Color result | light blond to copper-gold | copper-gold | light copper-colored | purple-brown | silver-blond | dark mahogany |

TABLE 6

Hair colorants

| | Example No. | | | | | |
|---|---|---|---|---|---|---|
| Dyes | 13 | 14 | 15 | 16 | 17 | 18 |
| | (Amount of dye in grams) | | | | | |
| 2-Amino-5-(3-thienyl)phenol hydrochloride | 0.10 | 0.05 | 0.01 | 0.005 | 0.270 | 0.010 |
| E8 | | | | 0.250 | | |
| E9 | | | | | 1.710 | 0.020 |
| E10 | | | | 2.000 | 0.200 | 0.010 |
| E15 | 0.70 | 0.70 | 0.70 | | | |
| K12 | 0.10 | 0.10 | 0.10 | | | |
| K13 | | | | | 0.100 | |
| K16 | | | | | | 0.015 |
| K21 | | | | | 0.800 | |
| K22 | | | | 1.800 | | 0.250 |
| K23 | 0.10 | 0.10 | 0.10 | | 0.200 | |
| K26 | | | | | | 0.030 |
| K31 | 0.40 | 0.40 | 0.40 | 0.250 | 0.135 | 0.020 |
| D2 | 0.10 | 0.10 | 0.10 | | 0.010 | |
| Color tone | brown | brown | brown | orange-colored | chocolate brown | silver-blond |

TABLE 7

| | Hair colorants | | | | | | | |
|---|---|---|---|---|---|---|---|---|
| | Example No. | | | | | | | |
| Dyes | 19 | 20 | 21 | 22 | 23 | 24 | 25 | 26 |
| | (Amount of dye in grams) | | | | | | | |
| 2-Amino-5-(3-thienyl)phenol hydrochloride | 0.01 | 0.18 | 0.04 | 0.18 | 0.18 | 0.18 | 0.06 | 0.18 |
| E8 | | 0.12 | | 0.12 | | | | |
| E9 | | | 0.12 | | 0.15 | | | |
| E15 | | | | | | 0.13 | | |
| W1 | 0.90 | | | 0.38 | | 0.38 | 0.38 | 0.38 |
| W2 | | 0.37 | 0.05 | | 0.58 | | | |
| Color | deep blue | mid-brown | mid-blond | black-brown | brown | black-brown | mid-brown | brown |

Unless stated otherwise, all of the percentages in the present application are percentages by weight.

The invention claimed is:

1. An agent for the oxidative coloring of keratin fibers based on a developer substance-coupler substance combination comprising at least one o-aminophenol derivative of the formula (I) or physiologically compatible, water-soluble salts thereof,

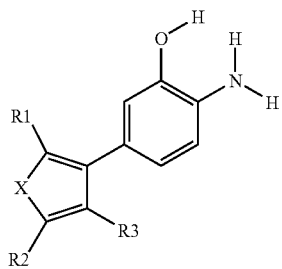

(I)

in which

X is oxygen, sulfur or N—R4;

R1, R2, R3 may be identical or different and, independently of one another, are hydrogen, a halogen atom, a cyano group, a $C_1$-$C_4$-alkoxy group, a $C_1$-$C_6$-alkyl group, a $C_1$-$C_4$-alkyl thioether group, a mercapto group, a nitro group, a trifluoromethane group, a —C(O)H group, a —C(O)CH$_3$ group, a —C(O)CF$_3$ group, an —Si(CH$_3$)$_3$ group, a $C_1$-$C_4$-hydroxyalkyl group or an aminomethyl group; and R4 is hydrogen, a $C_1$-$C_6$-alkyl group, a $C_1$-$C_4$-hydroxyalkyl group, a phenyl group or an acetyl group.

2. The agent as claimed in claim 1, wherein the o-aminophenol derivative of the formula (I) is present in an amount of from 0.001 to 5 percent by weight.

3. The agent as claimed in claim 1, wherein the agent has a pH of from 6.5 to 11.5.

4. The agent as claimed in claim 1, wherein the agent additionally comprises at least one dye from the group consisting of developer substances, coupler substances, direct dyes and other color components.

5. The agent as claimed in claim 1, wherein the agent is a hair colorant.

* * * * *